United States Patent
Luyken et al.

(10) Patent No.: US 6,252,115 B1
(45) Date of Patent: Jun. 26, 2001

(54) METHOD FOR SEPARATING AN IMINE FROM A MIXTURE CONTAINING AN AMINE AND AN IMINE

(75) Inventors: Hermann Luyken, Ludwigshafen; Peter Bassler, Viernheim; Alwin Rehfinger, Mutterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/341,948

(22) PCT Filed: Jan. 30, 1998

(86) PCT No.: PCT/EP98/00504

§ 371 Date: Jul. 21, 1999

§ 102(e) Date: Jul. 21, 1999

(87) PCT Pub. No.: WO98/34900

PCT Pub. Date: Aug. 13, 1998

(30) Foreign Application Priority Data

Feb. 7, 1997 (DE) .............................................. 197 04 614

(51) Int. Cl.⁷ ................................................. C07C 209/00
(52) U.S. Cl. ............................................................. 564/437
(58) Field of Search .............................. 564/437; 558/452

(56) References Cited

U.S. PATENT DOCUMENTS

| | | |
|---|---|---|
| 2,762,835 | 9/1956 | Swerdloff . |
| 3,696,153 | 10/1972 | Kershaw et al. . |
| 4,601,859 | 7/1986 | Galle et al. . |
| 5,153,351 | * 10/1992 | Sieja . |
| 5,162,567 | * 11/1992 | Sieja . |

FOREIGN PATENT DOCUMENTS

| | | |
|---|---|---|
| 954 416 | 12/1956 | (DE) . |
| 42 35 466 | 4/1994 | (DE) . |
| 195 00222 | 7/1996 | (DE) . |
| 195 48289 | 6/1997 | (DE) . |
| 893 709 | 4/1962 | (GB) . |
| 1041422 | 9/1966 | (GB) . |
| 1 238 351 | 7/1971 | (GB) . |
| 92/21650 | 12/1992 | (WO) . |
| 96/20166 | 7/1996 | (WO) . |
| 96/20931 | 7/1996 | (WO) . |

OTHER PUBLICATIONS

J. Arpe, Ind. Org. chem, Weissermel, 1986, 266.

* cited by examiner

Primary Examiner—Paul J. Killos
(74) Attorney, Agent, or Firm—Keil & Weinkauf

(57) ABSTRACT

A process for distillative separation of part or all of an imine (III) from a mixture (II) comprising an amine (I) and said imine (III) comprises adding to the distillation mixture a compound (IV) which is inert toward said amine (I) under distillation conditions and whose boiling point is above the boiling point of said amine (I) under said distillation conditions to obtain, after the distillation, a mixture (VI) comprising essentially said compound (IV).

10 Claims, No Drawings

METHOD FOR SEPARATING AN IMINE FROM A MIXTURE CONTAINING AN AMINE AND AN IMINE

The present invention relates to a process for distillative separation of part or all of an imine (III) from a mixture (II) comprising an amine (I) and said imine (III), which comprises adding to the distillation mixture a compound (IV) which is inert toward said amine (I) under distillation conditions and whose boiling point is above the boiling point of said amine (I) under said distillation conditions to obtain, after the distillation, a mixture (VI) comprising essentially said compound (IV).

Mixtures comprising an amine and an imine are customarily obtained in the hydrogenation of nitriles to amines.

The complete hydrogenation of adiponitrile to hexamethylenediamine, and also the partial hydrogenation with coproduction of hexamethylenediamine and 6-aminocapronitrile, in the presence of a catalyst based on a metal such as nickel, cobalt, iron, rhodium or ruthenium, is generally known, for example from: K. Weissermel, H.-J. Arpe, Industrielle Organische Chemie, 3rd Edition, VCH Verlagsgesellschaft mbH, Weinheim, 1988, page 266, U.S. Pat. Nos. 4,601,859, 2,762,835, 2,208,598, DE-A 848 654, DE-A 954 416, DE-A 42 35 466, U.S. Pat. No. 3,696,153, DE-A 19500222, WO 92/21650 and German Application 19548289.1.

By-products include imines such as aminohexylideneimine and tetrahydroazepine.

These imines, which, because of their color and deleterious effects on product properties, are undesirable impurities in the amines, which are customarily used for producing synthetic fibers, are difficult to separate from the amines.

For instance, GB-A-893 709 discloses installing a delay time vessel in the reflux line of a distillation column used for purifying hexamethylenediamine.

GB-A-1 238 351 describes the separation of hexamethylenediamine from mixtures comprising hexamethylenediamine and imines by addition of alkali metal hydroxide mixtures.

GB-A-1 041 442 discloses passing carbon dioxide into a distillation column used for separating hexamethylenediamine from mixtures comprising hexamethylenediamine and imines, during the distillation.

Disadvantages with the processes mentioned are the use of large vessels, which makes for reduced control of the distillation columns, and the formation of solids, which can lead to blockages.

It is an object of the present invention to provide a process for removing an imine from mixtures comprising an amine and an imine in a technically simple and economical manner.

We have found that this object is achieved by the process defined at the beginning.

Suitable amines I include aromatic amines such as benzylamine, aliphatic amines such as cyclic amines, for example isophoronediamine, or preferably acyclic amines, for example 1,4-diaminobutane, especially hexamethylenediamine or 6-aminocapronitrile, and also mixtures thereof.

Such amines can be prepared in a conventional manner.

For instance, hexamethylenediamine can be obtained by partial or complete catalytic hydrogenation with a gas comprising a molecular hydrogen, of adiponitrile to form hexamethylenediamine, or mixtures comprising hexamethylenediamine and 6-aminocapronitrile.

Suitable catalysts for this hydrogenation are advantageously those based on a metal selected from the group consisting of ruthenium, rhodium, nickel, cobalt and preferably iron, and the catalysts may contain further elements as promoters. In the case of iron-based catalysts, suitable promoters include especially one or more, such as two, three, four or five, elements selected from the group consisting of aluminum, silicon, zirconium, titanium and vanadium.

Such catalysts and process conditions for the reaction mentioned are described for example in WO-A-96/20166, German Application 19 636 768.9 and German Application 19 646 436.6.

The products obtained by the processes mentioned can subsequently be posthydrogenated with gases comprising molecular hydrogen, advantageously in the presence of catalysts based on nobel metals, such as platinum, palladium or mixtures thereof.

Suitable imines III include aromatic imines, aliphatic imines such as acyclic imines, in particular aminohexylideneimine, or cyclic imines, especially tetrahydroazepine of the formula

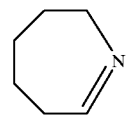

and also mixtures thereof.

The imines (III) can be present in the mixture (II) as individual compounds or as adducts, for example with an amine (I), in which case these adducts shall for the purposes of the present invention likewise be termed imines (III).

Such imines and processes for their preparation are generally known.

For instance, aminohexylideneimine and tetrahydroazepine can generally be obtained in amounts from 1 to 10000 ppm, based on the mixture, in mixtures (II) in the partial catalytic hydrogenation of adiponitrile with a gas comprising molecular hydrogen to form hexamethylenediamine or mixtures comprising hexamethylenediamine and 6-aminocapronitrile according to the processes described for the production of amines (I).

The invention provides that a compound (IV) which is inert to the amine (I) under distillation conditions and whose boiling point is above the boiling point of amine (I) under said distillation conditions be added to the distillation mixture.

Suitable compounds (IV) include aromatics, aliphatics, such as acyclic and cyclic aliphatics, and aliphatic-aromatic compounds. These compounds can bear substituents, such as a hydroxyl, keto, ester, alkyl, aryl, cycloalkyl or arylalkyl group, preferably a nitrile or amino group, or a plurality of identical or different such groups.

Said compound (IV) can consist of one compound or mixtures of such compounds.

It is advantageous to use compounds (IV) which are simple to convert, as by hydrogenation, for example with a gas comprising molecular hydrogen in the presence of a catalyst, into a mixture (V) comprising an amine (I) and an imine (III) or especially a mixture (II).

The products obtained in this reaction can advantageously be used afresh in the process of the invention.

The difference in the boiling points between the amine (I) and the compound (IV) should be from 1 to 200° C., preferably from 5 to 100° C., under distillation conditions.

If hexamethylenediamine is used as amine (I) and aminohexylideneimine, tetrahydroazepine or their mixtures as imine (III), then the use of adiponitrile, 6-aminocapronitrile or their mixtures is particularly advantageous.

If 6-aminocapronitrile is used as amine (I) and aminohexylideneimine, tetrahydroazepine or their mixtures as imine (III), then the use of adiponitrile or mixtures comprising essentially adiponitrile is particularly advantageous.

The compound (IV) can be added to the mixture (II) before or during the distillation.

The addition of compound (IV) to the mixture (II) before the distillation can be effected in a conventional manner in customary mixing apparatus.

The addition of the compound (IV) to the mixture (II) during the distillation can be effected by feeding the compound (IV) into the distillation apparatus, preferably in the bottom region.

Suitable apparatus for the distillation is any customary apparatus as described for example in Kirk-Othmer, Encyclopedia of Chemical Technology, 3rd Ed. Vol. 7, John Wiley & Sons, New York, 1979, pages 870–881, such as sieve plate columns, bubble cap columns or columns packed with arranged or dumped packing.

The distillation can be carried out in a plurality of columns, such as 2 or 3, but is advantageously carried out in a single column.

The distillation yields, preferably as bottom product, a mixture (VI) comprising essentially a compound (IV).

If the mixture (VI) additionally comprises amine (I), it is advantageously possible to reduce the bottom temperature of the distillation.

The compound (IV) can be recovered from the mixture (VI) in a conventional manner, for example by physical processes, such as distillation or extraction, or chemical processes, such as chemisorption or hydrogenation.

This compound (IV) obtained from the mixture (VI) can advantageously be recycled into the distillation of the invention.

Hexamethylenediamine can be processed with dicarboxylic acids such as adipic acid to form industrially important polymers.

We claim:

1. A process for distillative separation of part or all of an imine (III) selected from the group consisting of aminohexylideneimine, tetrahydroazepine or adducts thereof, from a mixture (II) comprising an amine (I) selected from the group consisting of hexamethylenediamine and 6-aminocapronitrile, and said imine (III), which comprises adding to the distillation mixture a compound (IV) which is inert toward said amine (I) under distillation conditions and whose boiling point is above the boiling point of said amine (I) under said distillation conditions to obtain, after the distillation, a mixture (VI) comprising essentially said compound (IV).

2. A process as claimed in claim 1, wherein said compound (IV) is added to said mixture (II) before the distillation.

3. A process as claimed in claim 1, wherein said compound (IV) is added to said mixture (II) during the distillation.

4. A compound as claimed in claim 1, wherein compound (IV) is a compound from which a mixture (V) comprising an amine (I) and an imine (III) or a mixture (II) is obtainable.

5. A process as claimed in claim 4, wherein, after the distillation, said compound (IV) is converted into a mixture (V) comprising essentially an amine (I) and an imine (III).

6. A process as claimed in claim 1, wherein amine (I) is hexamethylenediamine.

7. A process as claimed in claim 1, wherein imine (III) is selected from the group consisting of aminohexylideneimine, tetrahydroazepine, hexylhexahydroazepine and aminohexylhexahydroazepine.

8. A process as claimed in claim 1, wherein compound (IV) is adiponitrile, 6-aminocapronitrile or a mixture thereof.

9. A process as claimed in claim 1, wherein a compound (IV) is recovered from said mixture (VI).

10. A process as claimed in claim 1, wherein a compound (IV) is recovered from said mixture (VI) and recycled into the distillation.

* * * * *